United States Patent
Bar-Tal et al.

(10) Patent No.: US 10,105,117 B2
(45) Date of Patent: Oct. 23, 2018

(54) COMPENSATION FOR HEART MOVEMENT USING CORONARY SINUS CATHETER IMAGES

(71) Applicant: BIOSENSE WEBSTER (ISRAEL) LTD., Yokneam (IL)

(72) Inventors: Meir Bar-Tal, Haifa (IL); Omri Perez, Tel Aviv (IL); Aia Haruvi, Modiin-Maccabim-Reut (IL); Gay Kohen, Tel Aviv (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 356 days.

(21) Appl. No.: 14/621,570

(22) Filed: Feb. 13, 2015

(65) Prior Publication Data

US 2016/0235383 A1     Aug. 18, 2016

(51) Int. Cl.
| | |
|---|---|
| A61B 6/00 | (2006.01) |
| A61B 6/12 | (2006.01) |
| A61B 5/042 | (2006.01) |
| G06T 15/08 | (2011.01) |

(Continued)

(52) U.S. Cl.
CPC ............ *A61B 6/5235* (2013.01); *A61B 5/042* (2013.01); *A61B 5/0422* (2013.01); *A61B 6/12* (2013.01); *A61B 6/466* (2013.01); *A61B 6/487* (2013.01); *A61B 6/503* (2013.01); *G06T 7/38* (2017.01); *G06T 15/08* (2013.01); *G06T 19/20* (2013.01);
(Continued)

(58) Field of Classification Search
None
See application file for complete search history.

(56) References Cited

U.S. PATENT DOCUMENTS

| | | |
|---|---|---|
| 5,274,551 A | 12/1993 | Corby, Jr. |
| 5,546,951 A | 8/1996 | Ben Haim |
| 5,738,096 A | 4/1998 | Ben Haim |

(Continued)

FOREIGN PATENT DOCUMENTS

| | | |
|---|---|---|
| EP | 2168478 | 3/2010 |
| EP | 2732765 | 8/2014 |

(Continued)

OTHER PUBLICATIONS

Landau, L.D. et al., Electrodynamics of Continuous Media. Pergamon Pressm (1960) vol. 8, Sec. 45., pp. 189-190. of Course of Theoretical Physics, Textbook: ISBN No. 0-08-09105-9.

(Continued)

*Primary Examiner* — Jonathan Cwern
(74) *Attorney, Agent, or Firm* — Louis J. Capezzuto

(57) ABSTRACT

Cardiac catheterization is carried out by introducing a catheter into the coronary sinus, acquiring a first set of 2-dimensional images of the catheter, thereafter acquiring a second set of 2-dimensional images of the catheter, and creating respective 2-dimensional models of the catheter in synchronized frames of the first set and the second set. The 2-dimensional models include respective tracked 2-dimensional paths of the catheter. The first and second sets are synchronized by identifying frames that are in respective phases of the cardiorespiratory cycle. First and second 3-dimensional models of the catheter are constructed from the synchronized frames, and geometrically transformed to minimize a distance function between the two models.

25 Claims, 7 Drawing Sheets

(51) Int. Cl.
*G06T 19/20* (2011.01)
*G06T 7/38* (2017.01)

(52) U.S. Cl.
CPC .......... *A61B 2576/023* (2013.01); *G06T 2207/30048* (2013.01); *G06T 2219/2016* (2013.01)

(56) References Cited

U.S. PATENT DOCUMENTS

| | | | |
|---|---|---|---|
| 6,147,480 A | 11/2000 | Osadchy et al. | |
| 6,226,542 B1 | 5/2001 | Reisfeld | |
| 6,301,496 B1 | 10/2001 | Reisfeld | |
| 6,493,575 B1* | 12/2002 | Kesten | A61B 90/36 600/431 |
| 6,690,963 B2 | 2/2004 | Ben Haim | |
| 6,814,733 B2 | 11/2004 | Schwartz | |
| 6,892,091 B1 | 5/2005 | Ben Haim | |
| 6,997,924 B2 | 2/2006 | Schwartz | |
| 7,156,816 B2 | 1/2007 | Schwartz | |
| 7,536,218 B2 | 5/2009 | Govari et al. | |
| 7,756,576 B2 | 7/2010 | Levin | |
| 8,303,505 B2 | 11/2012 | Webler et al. | |
| 8,456,182 B2 | 6/2013 | Bar-Tal et al. | |
| 8,478,383 B2 | 7/2013 | Bar-Tal et al. | |
| 2004/0097805 A1* | 5/2004 | Verard | A61B 6/12 600/428 |
| 2007/0270692 A1* | 11/2007 | Barbu | A61B 6/12 600/431 |
| 2007/0276227 A1 | 11/2007 | Boese | |
| 2008/0091171 A1* | 4/2008 | Strommer | A61B 6/481 604/528 |
| 2009/0076483 A1 | 3/2009 | Danehorn | |
| 2009/0135992 A1 | 5/2009 | Vaillant et al. | |
| 2009/0163800 A1* | 6/2009 | Xu | A61B 6/12 600/424 |
| 2010/0256558 A1* | 10/2010 | Olson | A61M 25/0147 604/95.01 |
| 2011/0013816 A1* | 1/2011 | Gogin | A61B 5/113 382/128 |
| 2011/0069063 A1* | 3/2011 | Liao | G06T 7/33 345/419 |
| 2012/0075638 A1* | 3/2012 | Rollins | A61B 1/00009 356/479 |
| 2012/0165656 A1 | 6/2012 | Montag et al. | |
| 2012/0172712 A1 | 7/2012 | Bar-Tal | |
| 2012/0232384 A1 | 9/2012 | Wu et al. | |
| 2013/0072788 A1* | 3/2013 | Wu | G06T 7/277 600/424 |
| 2013/0184569 A1* | 7/2013 | Strommer | G06F 19/3437 600/424 |
| 2013/0231556 A1 | 9/2013 | Holsing et al. | |
| 2013/0301897 A1* | 11/2013 | Zhu | G06K 9/6207 382/132 |
| 2013/0324833 A1* | 12/2013 | Barley | A61B 6/12 600/424 |
| 2013/0331687 A1* | 12/2013 | Liao | A61B 5/061 600/424 |
| 2014/0016851 A1* | 1/2014 | Nakano | A61B 6/504 382/131 |
| 2014/0031676 A1* | 1/2014 | Nempont | A61B 6/12 600/424 |
| 2014/0221803 A1 | 8/2014 | Bar-Tal et al. | |
| 2015/0238159 A1* | 8/2015 | Al Assad | A61B 6/5258 378/5 |
| 2015/0313563 A1* | 11/2015 | Kelm | A61B 6/481 600/424 |
| 2016/0157751 A1* | 6/2016 | Mahfouz | A61B 5/062 600/409 |

FOREIGN PATENT DOCUMENTS

| | | |
|---|---|---|
| WO | WO 96/05768 A1 | 2/1996 |
| WO | WO 2007/138492 | 12/2007 |
| WO | WO 2013/036831 | 3/2013 |
| WO | WO 2013/057641 | 4/2013 |
| WO | WO 2014/124447 | 8/2014 |

OTHER PUBLICATIONS

Lindell, I.V. et al., Magnetostratic Image Theory for the Premeable Sphere, IEEE Transactions on Magnetics, (Jul. 1992) vol. 28, No. 4, pp. 1930-1934.
Extended European Search Report for EP16155496.9 Application, dated Jul. 6, 2016.
Extended European Search Report for EP16155431.6 Application, dated Jun. 29, 2016.
Co-pending U.S. Appl. No. 14/140,112, filed Dec. 24, 2013.
Felsberg, M. et al. The Monogenic Signal, IEEE Transactions on Signal Processing. vol. 49, No. 12, Dec. 2011, pp. 3136-3144.
Landau, L.D. et al. Electrodynamics of Continuous Media. Pergamon Press, 1960, vol. 8 of Course of Theoretical Physics, Textbook: ISBN No. 0-08-09105-9.
Loy, G. et al. A Fast Radial Symmetry Transform for Detecting Points of Interest. IEEE Transactions on Pattern Analysis and Machine Intelligence, Australian National University, Aug. 2003.

\* cited by examiner

COMPENSATION FOR HEART MOVEMENT USING CORONARY SINUS CATHETER IMAGES

BACKGROUND OF THE INVENTION

1. Field of the Invention

This invention relates to cardiac physiology. More particularly, this invention relates to the evaluation of electrical propagation in the heart.

2. Description of the Related Art

The meanings of certain acronyms and abbreviations used herein are given in Table 1.

TABLE 1

Acronyms and Abbreviations

| | |
|---|---|
| CS | Coronary Sinus |
| DetHes | Determinant of the Hessian |
| LAO | Left Anterior Oblique |
| RAO | Right Anterior Oblique |

Cardiac arrhythmias such as atrial fibrillation are an important cause of morbidity and death. Commonly assigned U.S. Pat. Nos. 5,546,951, and 6,690,963, both issued to Ben Haim and PCT application WO 96/05768, all of which are incorporated herein by reference, disclose methods for sensing an electrical property of heart tissue, for example, local activation time, as a function of the precise location within the heart. Data are acquired with one or more catheters having electrical and location sensors in their distal tips, which are advanced into the heart. Methods of creating a map of the electrical activity of the heart based on these data are disclosed in commonly assigned U.S. Pat. Nos. 6,226,542, and 6,301,496, both issued to Reisfeld, which are incorporated herein by reference. As indicated in these patents, location and electrical activity is typically initially measured on about 10 to about 20 points on the interior surface of the heart. These data points are then generally sufficient to generate a preliminary reconstruction or map of the cardiac surface. The preliminary map is often combined with data taken at additional points in order to generate a more comprehensive map of the heart's electrical activity. Indeed, in clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Catheters containing position sensors may be used to determine the trajectory of points on the cardiac surface. These trajectories may be used to infer motion characteristics such as the contractility of the tissue. As disclosed in U.S. Pat. No. 5,738,096, issued to Ben Haim, which is incorporated herein in its entirety by reference, maps depicting such motion characteristics may be constructed when the trajectory information is sampled at a sufficient number of points in the heart.

Electrical activity at a point in the heart is typically measured by advancing a multiple-electrode catheter to measure electrical activity at multiple points in the heart chamber simultaneously. A record derived from time varying electrical potentials as measured by one or more electrodes is known as an electrogram. Electrograms may be measured by unipolar or bipolar leads, and are used, e.g., to determine onset of electrical propagation at a point, known as local activation time.

SUMMARY OF THE INVENTION

Currently, large amounts of anatomical and functional data are gathered during catheter-based cardiac procedures. Maintaining alignment of this data with the actual position of the patient's heart is crucial. Extant solutions make use of electromagnetic sensors attached to the patient's back and chest to maintain this alignment. However, due in part to the elasticity of the human skin and internal movement of the viscera, this alignment is not always maintained. Such misalignment considerably hinders the cardiac procedure.

Embodiments of the invention enable tracking the patient's heart position during the medical procedure. When a catheter is placed in the coronary sinus, its position is closely related to the position of other portions of the heart. Therefore, estimating a transformation between coordinates of a coronary sinus catheter before and after a change in position enables the alignment to be accurately maintained.

In order to compensate for heart movement, an algorithm reconstructs the coronary sinus catheter in three dimensions, based on two 2-dimensional fluoroscopic images acquired before and after a movement. A transformation between the two reconstructed catheters is computed and used to align the data.

There is provided according to embodiments of the invention a method, which is carried out by introducing a catheter into a coronary sinus of a heart of a living subject. While the catheter is in the coronary sinus, the method is further carried out by acquiring a first set of frames including 2-dimensional images of the catheter, thereafter acquiring a second set of frames including 2-dimensional images of the catheter and establishing respective 2-dimensional models of the catheter in synchronized frames of the first and second sets. The 2-dimensional models include respective tracked 2-dimensional paths of the catheter. The method is further carried out by synchronizing the first set with the second set by identifying frames that are in respective phases of the cardiorespiratory cycle, constructing first and second 3-dimensional models of the catheter from the synchronized frames, geometrically transforming the first and second 3-dimensional models to minimize a distance function therebetween, and displaying the transformed 3-dimensional models.

According to another aspect of the method, geometrically transforming the 3-dimensional models is performed by applying a rotation matrix and a translation vector to one of the first and second 3-dimensional models and superimposing the transformed 3-dimensional models for display.

In another aspect of the method, wherein acquiring the first set and acquiring the second set each comprise acquiring frames at a first primary angle and at a second primary angle with the sagittal plane of the subject.

According to yet another aspect of the method, the first primary angle is 30° and the second primary angle is −30° with the sagittal plane of the subject.

One aspect of the method includes acquiring frames at the first primary angle and the second primary angle simultaneously.

In an additional aspect of the method establishing respective 2-dimensional models includes filtering the first set and the second set of frames, sampling a corridor about a catheter path in the filtered frames, and thereafter determining an optimal path of the catheter in the filtered frames.

According to one aspect of the method, filtering includes performing a fast radial transform on a determinant of a hessian of the synchronized frames.

According to a further aspect of the method, filtering includes applying monogenic filters on a determinant of a hessian of the synchronized frames.

According to yet another aspect of the method, filtering is performed by applying matched filters to tubes in the synchronized frames.

According to still another aspect of the method, constructing first and second 3-dimensional models includes constructing a chain of linear 3-dimensional segments connected by joints, and calculating 3-dimensional coordinates of the joints so as to minimize a deviation of a projection of the 3-dimensional segments onto the respective tracked 2-dimensional paths.

According to a further aspect of the method constructing a chain and calculating 3-dimensional coordinates are performed iteratively.

According to an additional aspect of the method establishing respective 2-dimensional models includes tracking a tip of the catheter in the synchronized frames, and constructing first and second 3-dimensional models includes initializing 3-dimensional coordinates of the tip.

Another aspect of the method constructing first and second 3-dimensional models is performed by defining a plurality of 3-dimensional points as intersections of respective projection rays, fitting a 3-dimensional spline to the 3-dimensional points to define a 3-dimensional path, projecting the 3-dimensional path onto one of the 2-dimensional models, and modifying the 3-dimensional path to minimize the distance function between the projected 3-dimensional path and the one 2-dimensional model.

There is further provided according to embodiments of the invention an apparatus, including a cardiac catheter adapted for introduction into a coronary sinus of a heart of a living subject, a display, and a processor, which is cooperative with a fluoroscopic imaging device for performing the above-described method.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program) instructions for conventional algorithms and processes have not been shown in detail in order not to obscure the general concepts unnecessarily.

Aspects of the present invention may be embodied in software programming code, which is typically maintained in permanent storage, such as a computer readable medium. In a client/server environment, such software programming code may be stored on a client or a server. The software programming code may be embodied on any of a variety of known non-transitory media for use with a data processing system, such as USB memory, hard drive, electronic media or CDROM. The code may be distributed on such media, or may be distributed to users from the memory or storage of one computer system over a network of some type to storage devices on other computer systems for use by users of such other systems.

System Overview.

Figure 1:
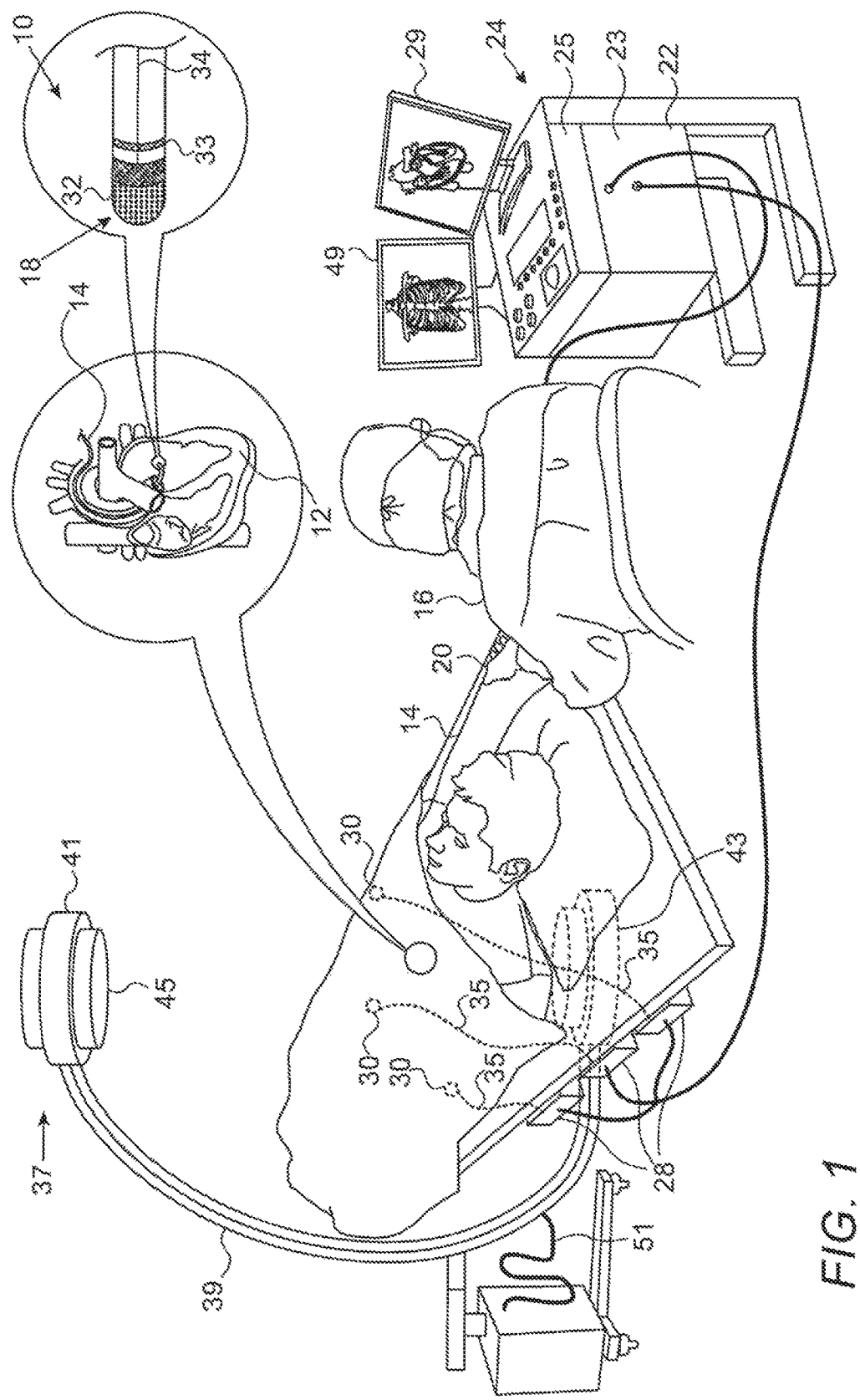
FIG. 1 is a pictorial illustration of a system for performing ablative procedures on a heart of a living subject, which is constructed and operative in accordance with an embodiment of the invention.

Turning now to the drawings, reference is initially made to FIG. 1, which is a pictorial illustration of a system 10 for performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall at an ablation target site. Electrical activation maps, anatomic positional information, i.e., of the distal portion of the catheter, and other functional images may then be prepared using a processor 23 located in a console 24, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, C.A. 91765, which is capable of producing electroanatomic maps of the heart as required for the ablation. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating (or cooling) it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in the console 24.

Ablation energy and electrical signals can be conveyed to and from the heart 12 through the catheter tip and/or one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning sub-system. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, freezing technique and laser-produced light energy. Such methods are disclosed in commonly assigned U.S. Pat. Nos. 6,814,733, 6,997,924, and 7,156,816, which are herein incorporated by reference.

The positioning processor 22 is an element of a positioning subsystem in the system 10 that measures location and orientation coordinates of the catheter 14.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem may employ impedance measurement, as taught, for example in U.S. Pat. No. 7,756,576, which is hereby incorporated by reference, and in the above-noted U.S. Pat. No. 7,536,218.

A fluoroscopic imaging device 37 has a C-arm 39, an x-ray source 41, an image intensifier module 43 and an adjustable collimator 45. A control processor (not shown), which may be located in the console 24, allows an operator to control the operation of the fluoroscopic imaging device 37, for example by setting imaging parameters, and controlling the collimator 45 to adjust the size and position of the field of view. The control processor may communicate with the fluoroscopic imaging device 37 via a cable 51 to enable and disable the x-ray source 41 or restrict its emissions to a desired region of interest by controlling the collimator 45, and to acquire image data from the image intensifier module 43. An optional display monitor 49, linked to the control processor, allows the operator to view images produced by the fluoroscopic imaging device 37. When the display monitor 49 is not included, the fluoroscopic images may be viewed on a monitor 29, either via a split screen or in alternation with other non-fluoroscopic images.

As noted above, the catheter 14 is coupled to the console 24, which enables the operator 16 to observe and regulate the functions of the catheter 14. The processor 23 is typically a computer with appropriate signal processing circuits. The processor 23 is coupled to drive the monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and analyze the electrical signals from the electrodes, and generate desired electroanatomic maps.

Typically, the system 10 includes other elements, which are not shown in the figures for the sake of simplicity. For example, the system 10 may include an electrocardiogram (ECG) monitor, coupled to receive signals from one or more body surface electrodes, to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided.

Operation.

Figure 2:
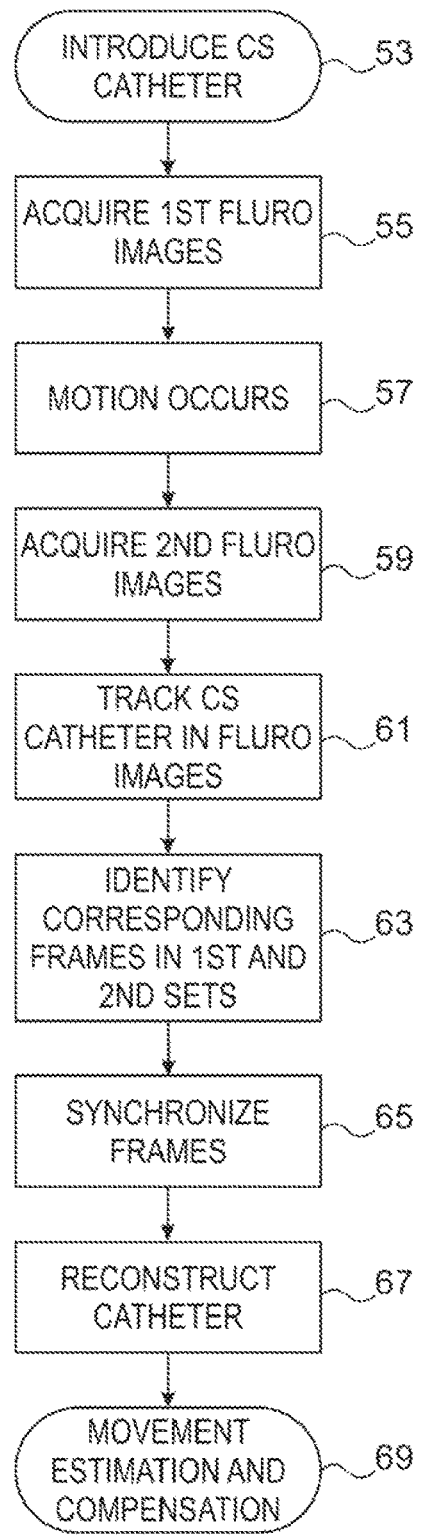
FIG. 2 is a flow-chart of a method of compensating heart movement during cardiac catheterization in accordance with an embodiment of the invention.

Reference is now made to FIG. 2, which is a flow-chart of a method of compensating heart movement during cardiac catheterization in accordance with an embodiment of the invention. The process steps are shown in a particular linear sequence for clarity of presentation. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the method.

At initial step 53 a catheter is introduced conventionally into the coronary sinus (CS).

Next, at step 55, a first set of sequential cinematographic fluoroscopic images of the heart, including the coronary sinus and the catheter is acquired at two angles similar to standard left and right anterior oblique views. This technique enabler 3-dimensional stereoscopic reconstruction of the catheters as described below. Primary angles of 30° and −30° with the sagittal plane of the patient's body are recommended. However, deviations are well tolerated, and the method is effective with a difference between primary angles varying up to 60°. A difference of 90° is theoretically optimum. Performance degrades beyond 90° and the method becomes ineffective when the difference exceeds 120°.

It is assumed that the geometry of the fluoroscope components is known. This is necessary in order to obtain an accurate 3-dimensional reconstruction of the region of interest in the heart. Moreover, tracking errors in magnetic sensors of the catheter resulting from changes in the positions of the magnetic field-perturbing fluoroscope components that are required to be moved when the two views are acquired may be compensated using the teachings of commonly assigned co-pending application Ser. No. 14/140,112, entitled Adaptive Fluoroscope Location for the Application of Field compensation, which is herein incorporated by reference.

Using standard stereoscopic methods, given the 3-dimensional image coordinates of a point and the camera positions, the point's position in space is determined as the intersection of the two projection rays (e.g., by triangulation).

Next, at step 57 the procedure continues, during which patient motion or heart motion occurs.

Next, at step 59 a second set of cinematographic fluoroscopic images is acquired, using the same technique as in step 55. All images in the two sets of images should be acquired at the same primary angles. As explained below, selected frames from the two sets are compared in the same respiratory phase and the same phase of the cardiac cycle. Thus at one phase of the cardiorespiratory cycle four frames are evaluated, a first pair of frames from the first set and second set at the first primary angle and a second pair of frames frame from the first set and the second set at the second primary angle. If this is not possible, then as a minimum members of each pair should be at the same phase of the cardio-respiratory respiratory cycle, respectively. The difference between the primary angles need not be the same for the first and second sets of fluoroscopic images. For example, the first set could be acquired at angles of −30° and 30° with the sagittal plane, and the second set could be acquired at angles of 0° and 60°.

Step 61 is a process for tracking the path of the coronary sinus catheter in the frames of the first and second sets of fluoroscopic images that were acquired in steps 55, 57.

Step 63 comprises a search among the two sets for frames taken at about the same cardio-respiratory phase. The search may comprise tracking 2-dimensional coordinates of the catheter among frames. At step 63 frames of the two sets in respective phases of the cardiorespiratory cycle are identified.

Cardio-respiratory phase synchronization among the views of the first and second set of images emulates a static scene and enables reconstruction using stereo image processing. Synchronization of this sort assures that the 3-dimensional shape and position of the catheter is nearly constant when captured by the fluoroscope at the two primary angles. Synchronization of the frames occurs in step 65. In practice perfect synchronization among sets of images is not feasible. Thus, it cannot be assumed that the scene is completely static. The available data for reconstruction are two 2-dimensional paths of the catheter. Determining corresponding points among the sets of images is termed "the correspondence problem" and is ubiquitous in computer vision. A reconstruction algorithm detailed below deals with this problem using numerical optimization methods.

Next in step 67 3-dimensional models of the catheter are reconstructed from the synchronized sets of images.

Then in final step 69 movement of the catheter between the sets of images is determined and compensated to align with data being displayed in association with the coronary sinus catheter. Details of steps 65, 63, 67, 69 are presented below.

2-Dimensional Tracking.

Figure 3:
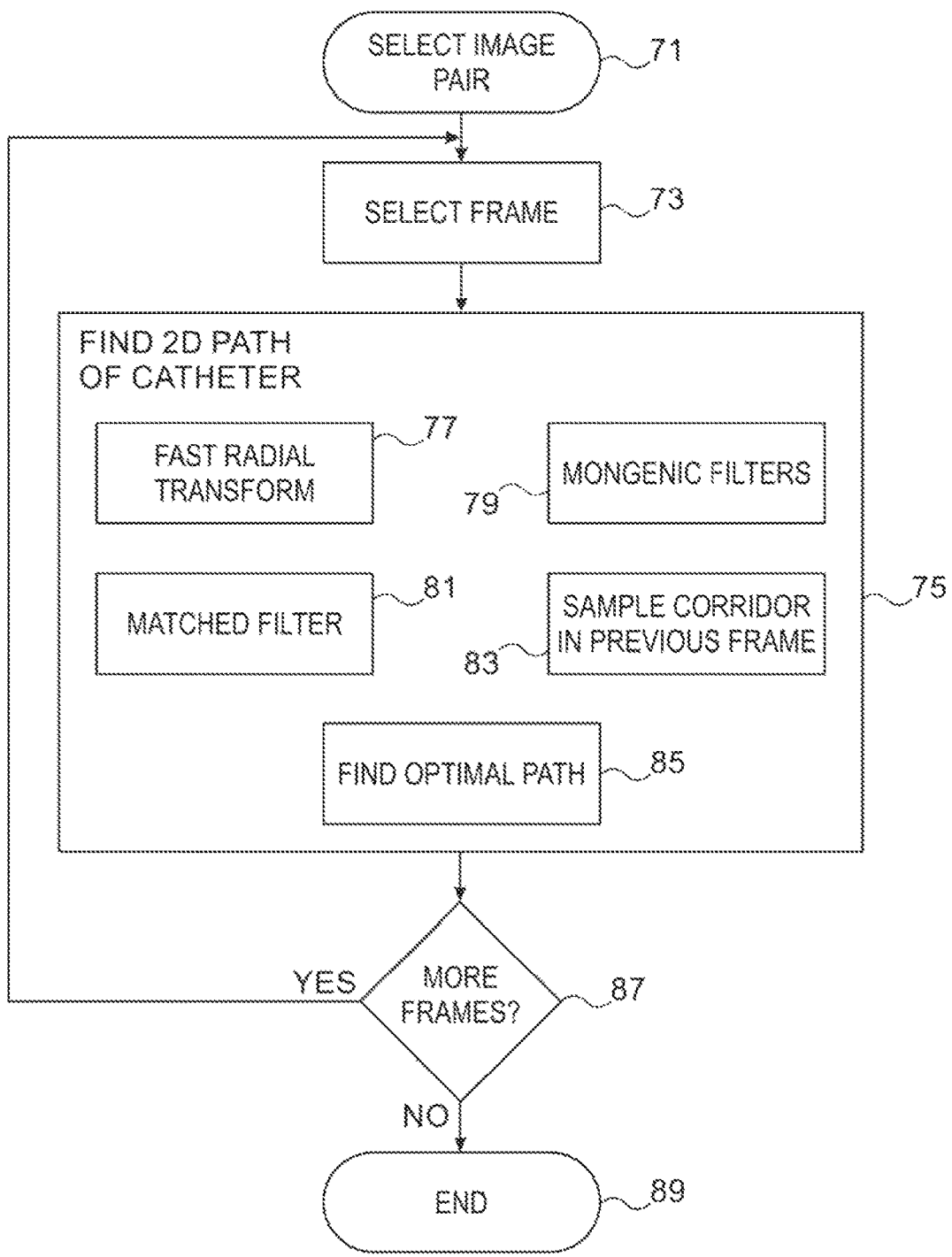
FIG. 3 is a flow-chart of a method for tracking the 2-dimensional path of a coronary sinus catheter in accordance with an embodiment of the invention.

Reference is now made to FIG. 3, which is a detailed flow-chart of step 61 (FIG. 2). The flow-chart is a frame-by-frame method for tracking the 2-dimensional path of a coronary sinus catheter in accordance with an embodiment of the invention. The method is applied to frames of the first and second sets that were produced in steps 55, 59 (FIG. 2).

At initial step 71 it is assumed that the search described in step 61 has been performed A group of images taken at one of the primary angles is selected for further reconstruction. As noted above members of the group are synchronized in the cardio-respiratory cycle.

Next, at step 73 a frame is selected from the images chosen in initial step 71.

Next, at step 75 the 2-dimensional path of the coronary sinus catheter is tracked in the current frame. In the first iteration of step 75 the operator marks points in an initial frame to indicate the position of the coronary sinus catheter, which needs to be distinguished from other catheters in the image as well as wires belonging to ECG leads and body surface location sensors. Using the markings the 2-dimensional contour of the coronary sinus catheter (referred to herein as a "path") is identified in the image. The 2-dimensional configuration is applied to subsequent frames to search for and locate the catheter. If possible, the image sequence should be acquired for a sufficiently long duration of time in order to cover at least one cardiorespiratory cycle. Step 75 comprises procedures that emphasize the catheter in the frame.

In block 77 a fast radial transform is performed on the determinant of the hessian of the image (DetHes)). The transform facilitates detection of radial regions in the image, such as the catheter electrodes. The fast radial transform is known from the document Loy & Zelinsky, *Fast Radial Symmetry for Detecting Points of Interest*, IEEE Transactions on Pattern Analysis and Machine Intelligence, August 2003.

In block 79 phase symmetry of the image is characterized by applying monogenic filters on the DetHes. This facilitates detection of regions with bilateral phase symmetry, catheters and catheter electrodes (see image 95, FIG. 4). Monogenic filters are known from the document Michael Felsberg and Gerald Sommer. *The Monogenic Signal*, IEEE, Transactions on Signal Processing, 49(12):3136-3144, December 2001, In block 81 a matched filter is applied for tubes in all orientations. The width of the matched filter is the estimated diameter of the catheter in pixels in the image. This procedure detects tubular regions with a specified diameter (see image 97, FIG. 4).

In block 83 a corridor is sampled from the filtered image (image 99, FIG. 4) around the location of the catheter path or contour obtained in the performance of step 75 on the previous frame. In the first iteration of step 75 the operator's marking is used (see image 101, corridor 103; image 109; FIG. 5).

In block 85 using dynamic programming methods known in the art, the optimal path in the sampled corridor is found (see image 111, FIG. 5). This path (dotted line in image 113; FIG. 5) is translated back into image coordinates.

Control now proceeds to decision step 87, where it is determined if more frames remain to be processed. If the determination at decision step 87 is affirmative, then control returns to step 73 to iterate the process with the next frame.

If the determination at decision step 87 is negative then control proceeds to final step 89 and the procedure terminates.

Figure 4:
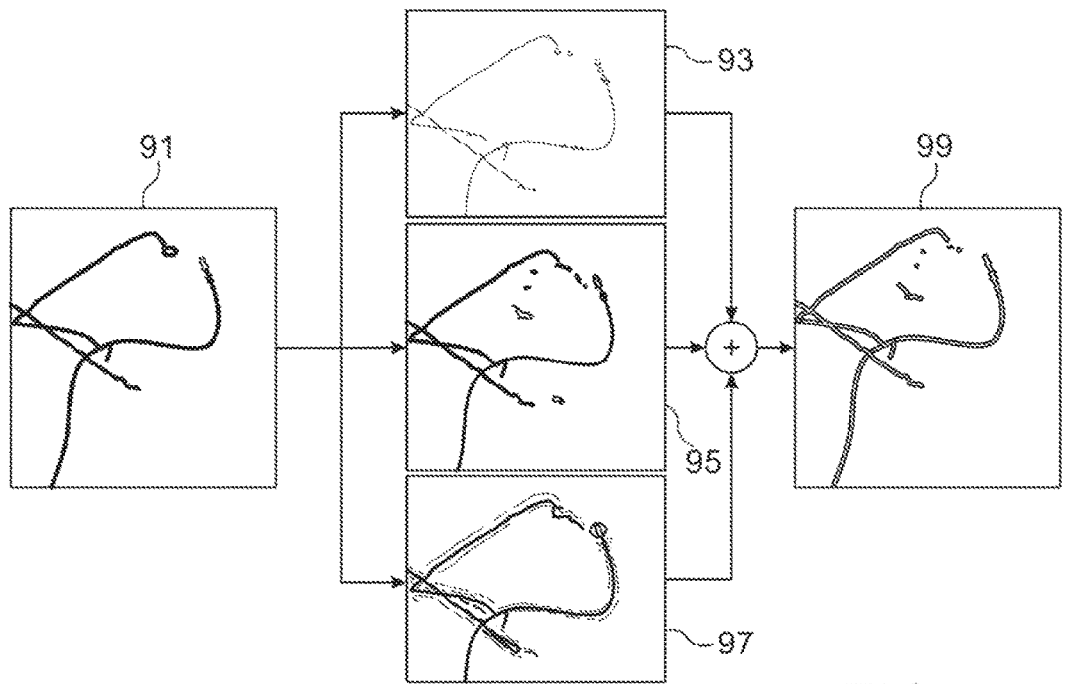
FIG. 4 is a collection of image frames that illustrate aspects of the method shown in FIG. 3 in accordance with an embodiment of the invention.
Figure 5:
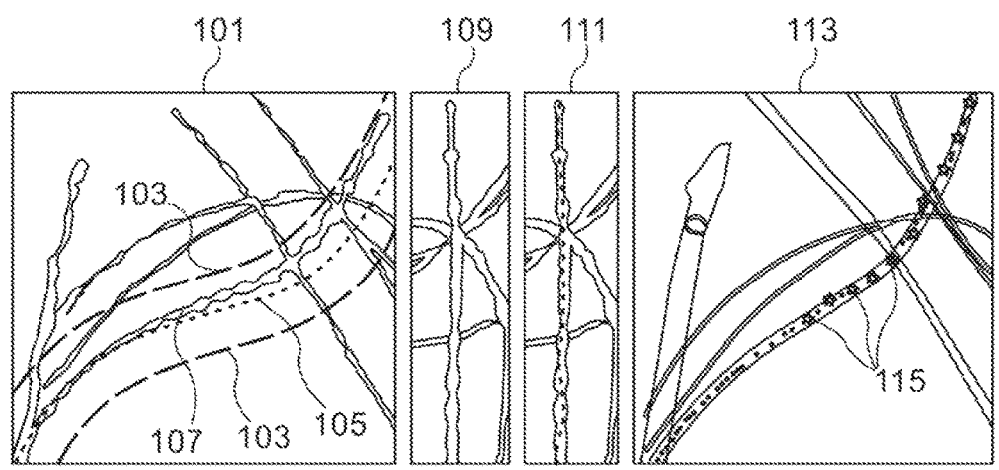
FIG. 5 is a sequence of images that illustrate aspects of the method shown in FIG. 3 in accordance with an embodiment of the invention.

Reference is now made to FIG. 4, which is a collection of frame images that graphically illustrate step 75 (FIG. 3) in accordance with an embodiment of the invention. Image 91 shows cardiac catheters in situ prior to filtering procedures. Image 93 is a version of the image 91 following a fast radial transform. Image 95 is a version of the image 91 following monogenic filtering. Image 97 is a version of the image 91 following a matched filtering operation. Image 99 is a version of the image 91 after additively combining the filtering operations that produced images 93, 95, 97. The image 99 is sampled to tentatively identify the location of the path of the coronary sinus catheter.

Reference is now made to FIG. 5, which is a sequence of images in accordance with an embodiment of the invention, which illustrate the tracking procedure, i.e., the dynamic programming operation described with respect to block 85 (FIG. 3). The images in FIG. 5 were produced by the filtering processes that produced the image 99 (FIG. 4). In image 101 a corridor 103 is outlined and sampled around the catheter path 105 (represented by a broken line). The path 105 was annotated in a previous frame (or by the operator, as noted above). It will be noted that the path 105 diverges from the coronary sinus catheter 107. Movement of the catheter 107 has occurred since the previous frame as the cardiorespiratory cycle has advanced. Image 109 illustrates sampled corridor. Image 111 illustrates the catheter path of the sampled corridor in image 109 as determined by dynamic programming. Image 113 shows a catheter path produced by dynamic programming along which are found a series of estimated electrode locations 115.

Synchronization.

When considering the 2-dimensional path of the catheter during the cinematographic image sets, we see that the catheter is constantly moving due to the patient's heartbeat and breathing. In order to reconstruct the catheter successfully in step 65 (FIG. 2), we find two frames (one from each clip) that were taken in approximately the same phase. In order to find those frames, we look for the coincidence of ventricular diastole and end-exhalation, at which the catheter is relatively motionless compared to other phases of the cardiorespiratory cycle. Using primary angles close to LAO and RAO and negligible secondary angles at this coincidence, the catheter tip position is typically observed at an extreme proximity to the bottom and to the right of conventionally displayed fluoroscopic images. For this purpose, secondary angles refer to orbital angles about an axis of movement of the C-arm 39 (FIG. 1), e.g., the cranio-caudal axis.

Figure 6:
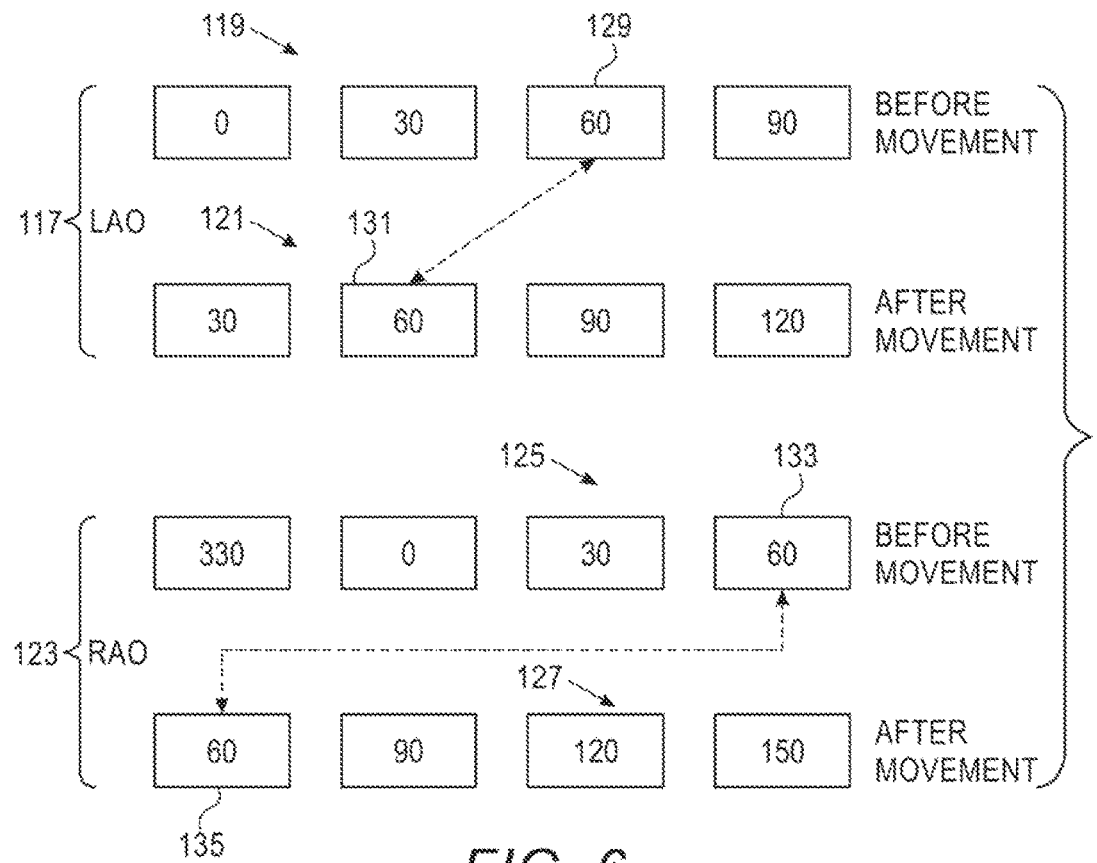
FIG. 6 is a diagram illustrating selection of image frames for reconstruction of a coronary sinus catheter in accordance with an embodiment of the invention.

Reference is now made to FIG. 6, which is a diagram illustrating selection of frames for use in reconstruction of a coronary sinus catheter in accordance with an embodiment of the invention. Set 117 of cinematographic images taken in the LAO projection comprises two series 119, 121 of frames taken before and after patient movement, respectively. Set 123 of cinematographic images taken in the RAO projection comprise two series 125, 127 of frames taken before and after patient movement, respectively. The phase of the cardiorespiratory cycle of each of the frames in FIG. 6 is denoted by a numerical value. It will be understood that these values are intentionally simplified for purpose of explication, the cardiorespiratory cycle actually being a more complex combination of the cardiac cycle and the respiratory cycle.

In searching among the frames of the set 117, it will be appreciated that the series 119, 121 are 30° out of phase. However frames 129, 131 are in phase with one another and are suitable for use in the reconstruction algorithm described below. Similarly in the set 123 the series 125, 127 are 90° out of phase. However frames 133, 135 are in phase with one another and are suitable for use in the reconstruction algorithm.

Reconstruction.

After synchronizing and finding two frames in which the coronary sinus catheter is approximately at the same phase, we can assume that a 3-dimensional point is the intersection of the projection rays (triangulation). However, instead of corresponding 2-dimensional points there are 2-dimensional paths. The correspondence of 2-dimensional points of the catheter on successive frames is not known. A best-fitting 3-dimensional model of the catheter is constructed for a synchronized pair of 3-dimensional frames. Reconstruction is carried out in step 67 (FIG. 2). Three reconstruction algorithms are presented herein.

I. Iterative Reconstruction with Linear Segments.

One method of constructing the 3-dimensional model utilizes a catheter model that consists of a chain of linear 3-dimensional segments with a constant length connected by joints. The parameters that specify the model are:
 1. The 3-dimensional position of tip (tipPos).
 2. The segment length (constant, L).
 3. The orientation of each segment relative to the previous segment (two angles—spherical coordinates, $\alpha$, $\beta$).

In order to calculate the 3-dimensional coordinates of the joints, we need to generate rotation matrices using the two orientation angles ($\alpha$, $\beta$) for each joint. The rotation matrix that defines the orientation of the segment that is connected to joint n is defined as following:

$$R_n = R_n^z * R_n^x = \begin{pmatrix} \cos\beta_n & -\sin\beta_n & 0 \\ \sin\beta_n & \cos\beta_n & 0 \\ 0 & 0 & 1 \end{pmatrix} * \begin{pmatrix} 1 & 0 & 0 \\ 0 & \cos\alpha_n & -\sin\alpha_n \\ 0 & \sin\alpha_n & \cos\alpha_n \end{pmatrix}$$

After building the rotation matrices for all of the joints, we can generate the 3-dimensional coordinates of the joints in the following manner:

$$\text{Joint}_n = R_{n-1} R_{n-2} \ldots R_2 R_1 * \begin{pmatrix} 0 \\ 0 \\ L \end{pmatrix} + \text{Joint}_{n-1}$$

$$\text{Joint}_1 \stackrel{def}{=} tipPos.$$

The process of finding the specific shape and position of a catheter is iterative. First, using the known camera positions and the image coordinates of the tip (first electrode of the catheter), we initialize the catheter's 3-dimensional position as the intersection of the projection rays (triangulation). Afterwards, in an iterative process, we find the orientation of each linear segment such that its projection is closest to the tracked 2-dimensional paths (analogous to external energy of a thermodynamic system). To constrain the 3-dimensional model to resemble a real catheter we also minimize the catheter's 3-dimensional curvature (analogous to internal energy). The terms "external energy" and "internal energy" are used for convenience to describe the linear segments in the discussion below.

In other words, we search for a 3-dimensional catheter model whose projections on the image are as close as possible to the tracked 2-dimensional paths tracked and which has minimal 3-dimensional curvature.

Figure 7:
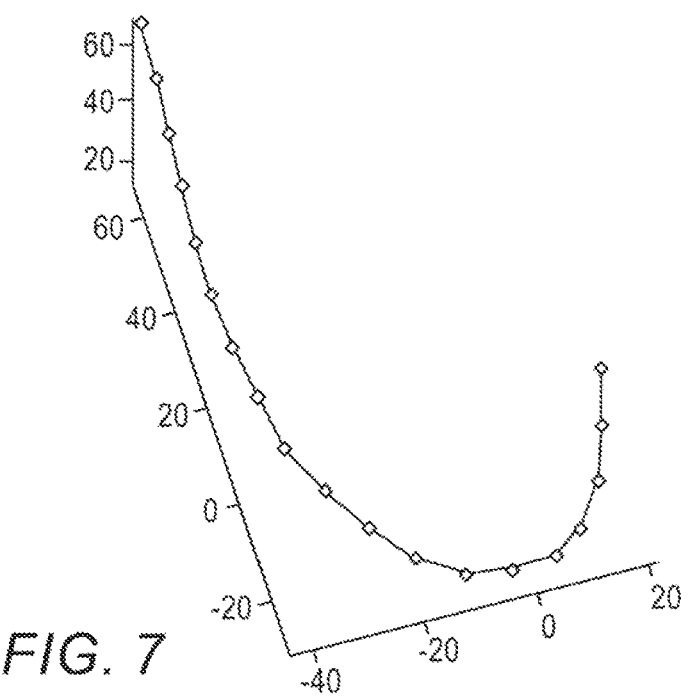
FIG. 7 is a graphical representation of a coronary sinus catheter that was produced by construction of linear segments in accordance with an embodiment of the invention.

Reference is now made to FIG. 7, which is a graphical representation of a coronary sinus catheter that was produced by construction of linear segments method in accordance with an embodiment of the invention.

In the following, we describe internal and external energies, optimization targets and a schedule of optimization:

External Energy.

The external energy of the 3-dimensional catheter model reflects the distance between the joints of the linear segments, projected onto the two 2-dimensional fluoroscope planes, and the two 2-dimensional tracked catheter paths.

First we define a function that takes the parameter vector θ of the 3-dimensional catheter model (tip position, and 2 angles per joint) and returns m 3-dimensional points corresponding to the joints of the 3-dimensional catheter:

$$g(\theta){:}\theta \to R^{m \times 3}.$$

Then we define a function that projects the 3-dimensional locations of the in joints of the 3-dimensional catheter to the two fluoroscopic image planes:

$$f_1{:}R^{m \times 3} \to R^{m \times 2}$$

$$f_2{:}R^{m \times 3} \to R^{m \times 2}.$$

Next we define a function that estimates the soft-minimum distance of each of the projected joints to the n two-dimensional points along the catheter path in each of the fluoroscopic image planes (points1, points2):

$$d\_soft(joints, pnts)_i{:}(R^{m \times 2}, R^{n \times 2}) \to R^{m \times 1}$$

$$d\_soft(joints, pnts)_i = \underset{j}{softmin} \left\| \overrightarrow{joints^i} - \overrightarrow{pnts^j} \right\|.$$

We use the soft-min (and soft-max below) to ensure that the derivatives are continuous throughout the optimization process. The soft-min (or max function) is defined as following:

$$S_k(\{x_i\}_{i=1}^n) = \frac{\sum_{i=1}^n x_i e^{kx_i}}{\sum_{i=1}^n e^{kx_i}}.$$

When $k \to +\infty$ the function approximates the hard-max and when $k \to -\infty$ it approximates the hard-min. For soft-min we use $k=-1$ and for soft-max we use $k=1$.

Finally, we define the external energy:

$$ext(\theta) = \frac{1}{m+n}\left(\sum_i^m d_{soft(f_2(g(\theta)_{ipoints1}))_i}^2 + \sum_i^n d_{soft(f_2(g(\theta)_{ipoints2}))_i}^2\right)$$

Internal Energy.

Next we define the internal energy. The purpose of the internal energy is to constrain the evolving 3-dimensional model of the catheter so that it has a smooth shape in 3-dimensions and does not "bend" too much.

First we define a tangent function for the angle between two unit direction vectors. We define the unit direction vectors to be the vectors from one joint to the next:

$$\hat{v}_i = \frac{joints^i - joints^{i-1}}{\|joints^i - joints^{i-1}\|}$$

$$\tan(\hat{v}_i, \hat{v}_{i-1}) = \frac{\hat{v}_i \times \hat{v}_{i-1}}{(\hat{v}_i \cdot \hat{v}_{i-1}) + c_1},$$

Where $c_1$ is a small constant that prevents division by zero. The tan is discontinuous at $\pi/2$. To alleviate this caveat, we define the following continuous function:

$$ContinuousTangent(\hat{v}_i, \hat{v}_{i-1}) = (1 - w(\hat{v}_i, \hat{v}_{i-1}))*\tan(\hat{v}_i, \hat{v}_{i-1}) + w(\hat{v}_i, \hat{v}_{i-1})*c_2$$

Where w is a sigmoidal function and $c_2$ is a large coefficient that replaces the value of the tangent at large angles. The function w is defined as:

$$w(\hat{v}_i, \overrightarrow{v_{i-1}}) = 1/(1 + e^{-(a*(\|\hat{v}_i - \hat{v}_{i-1}\|)+b)}),$$

Where a and b are selected so that the sigmoidal functions departs 0 at $\pi/3$ and approaches 1 at $\pi/2$.

Finally, the internal energy is defined as follows:

$$int(\theta) = \underset{i}{softmax}(ContinuousTangent(\hat{v}_i, \hat{v}_{i-1})^2).$$

Iterative Optimization.

To iteratively reconstruct the catheter, do the following:
(1) Find the 3-dimensional tip position using triangulation from the tracked 2-dimensional positions in both fluoroscopic images.
(2) Add a segment to the growing end of the 3-dimensional model. The segment is added so that its direction vector points in the same direction as the previous segment ($\alpha=0$, $\beta=0$). Then optimize these angles to minimize the external and internal energy.
(3) After optimizing the last joint, optimize all of the joints (including the tip) added so far to the model.
(4) Repeat step 2 until the projection of the 3-dimensional model covers the entire 2-dimensional path of the catheter, in at least one fluoroscopic image.

The optimization target (for both stages 2 and 3) is as follows:

$$\underset{\theta}{min}(\lambda_1 * int(\theta) + \lambda_2 * ext(\theta))'$$

where the different λ represent the weight of the errors.

II. Fluoroscopic Image Based Iterative Reconstruction with Linear Segments.

This algorithm is similar to the previous algorithm (Iterative Reconstruction With Linear Segments) in that it relies on the linear segment 3-dimensional catheter model and iterative reconstruction. However, instead of relying on the tracking to describe the 2-dimensional paths of the catheter, the algorithm relies on the fluoroscopic images themselves. This eliminates the need for tracking the entire catheter and reduces the chances for error and saves time. Now we only need to track the tip of the catheter throughout the cinematographic frames for the purpose of synchronization and for initializing the 3-dimensional tip position of the model. Next, iterative addition of linear segments is performed so that their projection lies on a position in the image that most looks like a catheter. Using the matched filter described above (block 81, FIG. 3) enables us to detect regions that look most like a catheter and thus facilitate the optimization process. The iterative optimization is identical to the previous embodiment, except for the external cost function. In this embodiment the distance is measured against points in the image that are candidates for catheter location, i.e., have a strong response in the filter.

III. Global Reconstruction Using Epi-Polar Geometry.

This algorithm starts with finding a global initial guess for the 3-dimensional catheter path by performing triangulation of matched points (finding in 3-dimensional space the point at the intersection of the projection rays) and then using an optimization process to get the final catheter model. The matching process is based on epi-polar geometry, which is well-known in the art.

Figure 8:
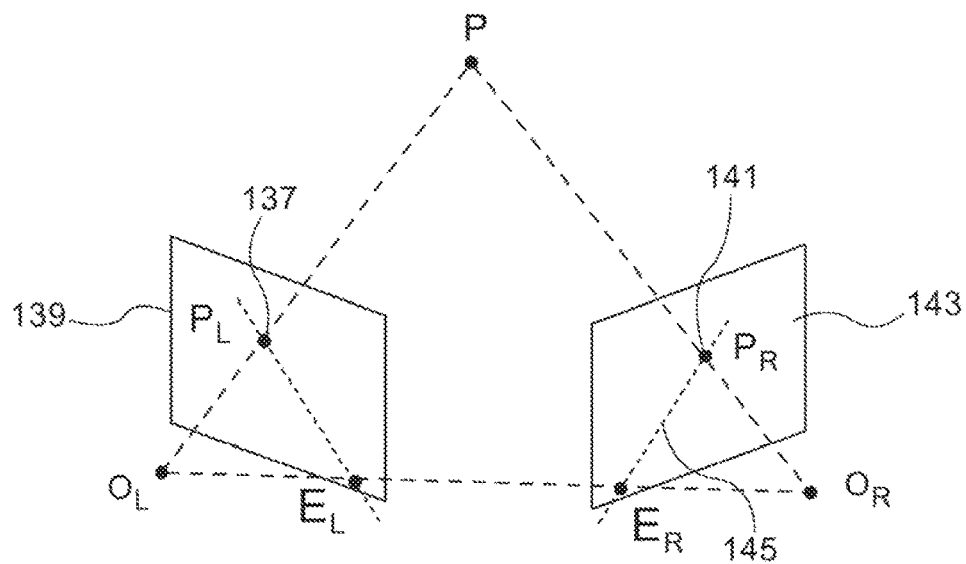
FIG. 8 is a diagram explaining the use of epi-polar geometry in accordance with an embodiment of the invention.

Reference is now made to FIG. 8, which is a diagram explaining the application of epi-polar geometry in accordance with an embodiment of the invention. The matching process relies on the fact that given an image point 137 from a first image 139 and the exact geometry of the cameras (not shown), a corresponding point 141 on a second image 143 will be on a specific 2-dimensional line 145 in the image 143.

Figure 9:
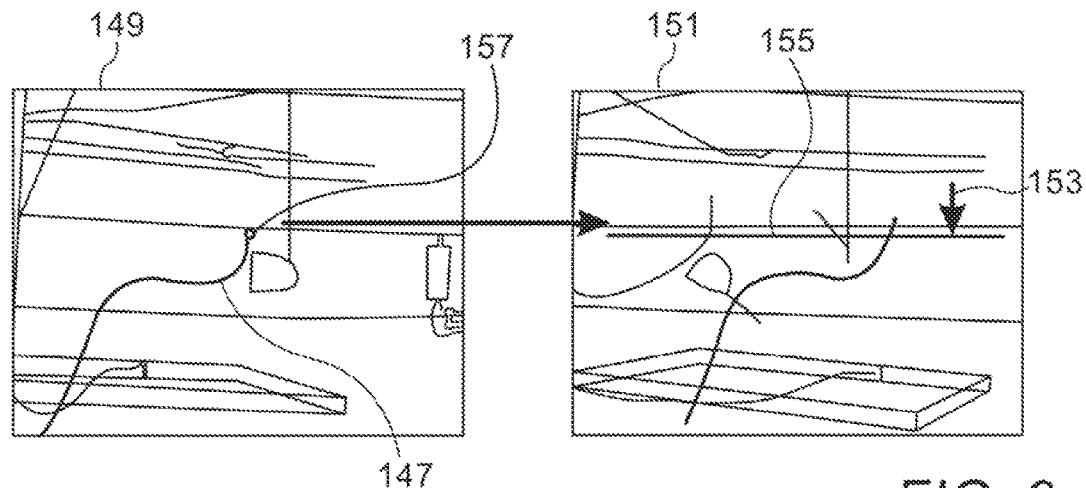
FIG. 9 presents two diagrams that schematically illustrate a stage of reconstruction using epi-polar geometry in accordance with an embodiment of the invention.

Reference is now made to FIG. 9, which presents two diagrams that schematically illustrate a stage of reconstruction using epi-polar geometry in accordance with an embodiment of the invention. Because the synchronization process described above is not exact, a 2-dimensional path 147 of one frame 149 of a corresponding 2-dimensional pair of frames is shifted vertically, based on a known 2-dimensional point, (i.e., the tip of the catheter) in order to force the other frame 151 of the pair to conform to epi-polar theory. The vertical displacement is indicated by arrow 153 on the frame 151 Put differently, we shift the 2-dimensional path vertically in arrow 153, so that the tip will lie on epi-polar line 155 induced by the catheter tip in the frame 149. The epi-polar line 155 is calculated from a point 157 in the frame 149.

For each corresponding pair of frames, we find the 3-dimensional point as the intersection of the projection rays and fit a smooth 3-dimensional spline (parameterized by θ) to these points. Then, we project the 3-dimensional spline to the two 2-dimensional image planes. We then modify the 3-dimensional spline so as to minimize the distances between the 2-dimensional projections and the 2-dimensional path. Following is a description of this minimization procedure:

First define a function that takes the parameter vector θ of the 3-dimensional spline and returns a collection of m 3-dimensional points sampled along the spline:

$$g(\theta): \theta \rightarrow R^{3 \times m}.$$

Next define two functions that project the 3-dimensional points to the two fluoroscopic planes:

$$f_1: R^{3 \times m} \rightarrow R^{2 \times m}$$

$$f_2: R^{3 \times m} \rightarrow R^{2 \times m}$$

From the tracking results, we get a collection of 2-dimensional points along the catheter path in each of the fluoroscope planes: points1, points2

Now we define a function that finds the minimum distances between one 2-dimensional point set to another (asymmetric)

$$d(P_1, P_2)_i : (R^{m \times 2}, R^{n \times 2}) \rightarrow R^{m \times 1}.$$

$$d(P_1, P_2)_i = \min_j \left\| \vec{P_1^i} - \vec{P_1^j} \right\|$$

Conversely, the mean bidirectional (symmetric) distance between two 2-dimensional point sets is:

$$D_{bi}(P_1, P_2) = \frac{1}{m+n} \left( \sum_i^m d(P_1, P_2)_i + \sum_i^n d(P_2, P_1)_i \right).$$

Finally we perform the optimization:

$$\min_\theta (D_{bi}(f_1(g(\theta)), \text{points1}) + D_{bi}(f_1(g(\theta)), \text{points2}))'$$

Movement Estimation.

Having reconstructed the two 3D models of the catheter, we can calculate the transformation between them. We assume that the transformation consists solely of rotation and translation (R, T). Expecting the same 3D shape/curve, we force the two catheters to be of the same length (using their curvatures, we cut the excess tail region of the longer catheter). Using an optimization process, we find the rotation and translation that minimizes the distances between the catheters. Movement estimation is carried out in final step 69 (FIG. 2).

P1 and P2 describe 3D points along the two reconstructed catheters. As before we define an asymmetric distance function that finds the minimum distances between one 3D point-set to another:

$$d(P_1, P_2)_i : (R^{m \times 3}, R^{n \times 3}) \rightarrow R^{m \times 1}$$

$$d(P_1, P_2)_i = \min_j \left\| \vec{P_1^i} - \vec{P_1^j} \right\|$$

We also define, the mean bidirectional (symmetric) distance between two 3D point sets (that belong to the two catheters) as:

$$D_{bi}(P_1, P_2) = \frac{1}{m+n} \left( \sum_i^m d(P_1, P_2)_i + \sum_i^n d(P_2, P_1)_i \right).$$

To find the correct transformation between the two catheters, we minimize:

$$\min_{R,T} D_{bi}(P_1, R * P_2 + T)^2$$

Figure 10:
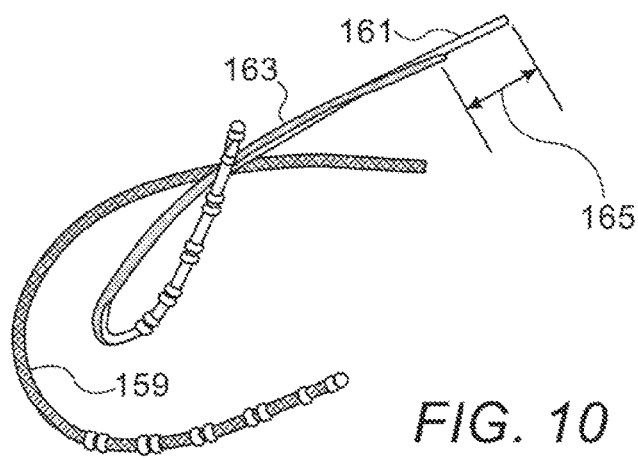
FIG. 10 is a diagram illustrating a process of movement estimation of a coronary sinus catheter in accordance with an embodiment of the invention.

It is this transformation that enables us to deduce the change in the position of the patient's heart. Reference is now made to FIG. 10, which is a diagram illustrating a process of movement estimation of a coronary sinus catheter in accordance with an embodiment of the invention. Three catheter images 159, 161, 163 are shown. Image 159 represents a catheter in a first frame of a cinematographic series. Image 161 represents the catheter in a second frame of the series. Translational and rotational displacement have occurred. Image 163 represents the result of transforming the image 159 using the algorithm described above. It will be evident that in the display the image 163 is approximated to the image 161 as closely as possible, i.e., nearly superimposed on the image 161. In addition to translation and rotation, in the image 163 there is truncation of tail segment 165 of the image 161. Displaying the transformed images to the operator compensates for the motion and enables the operator to view data that is associated with the catheter without having to cope with disturbing motion effects caused by cardiac and respiratory movements.

Alternate Embodiment

Figure 11:
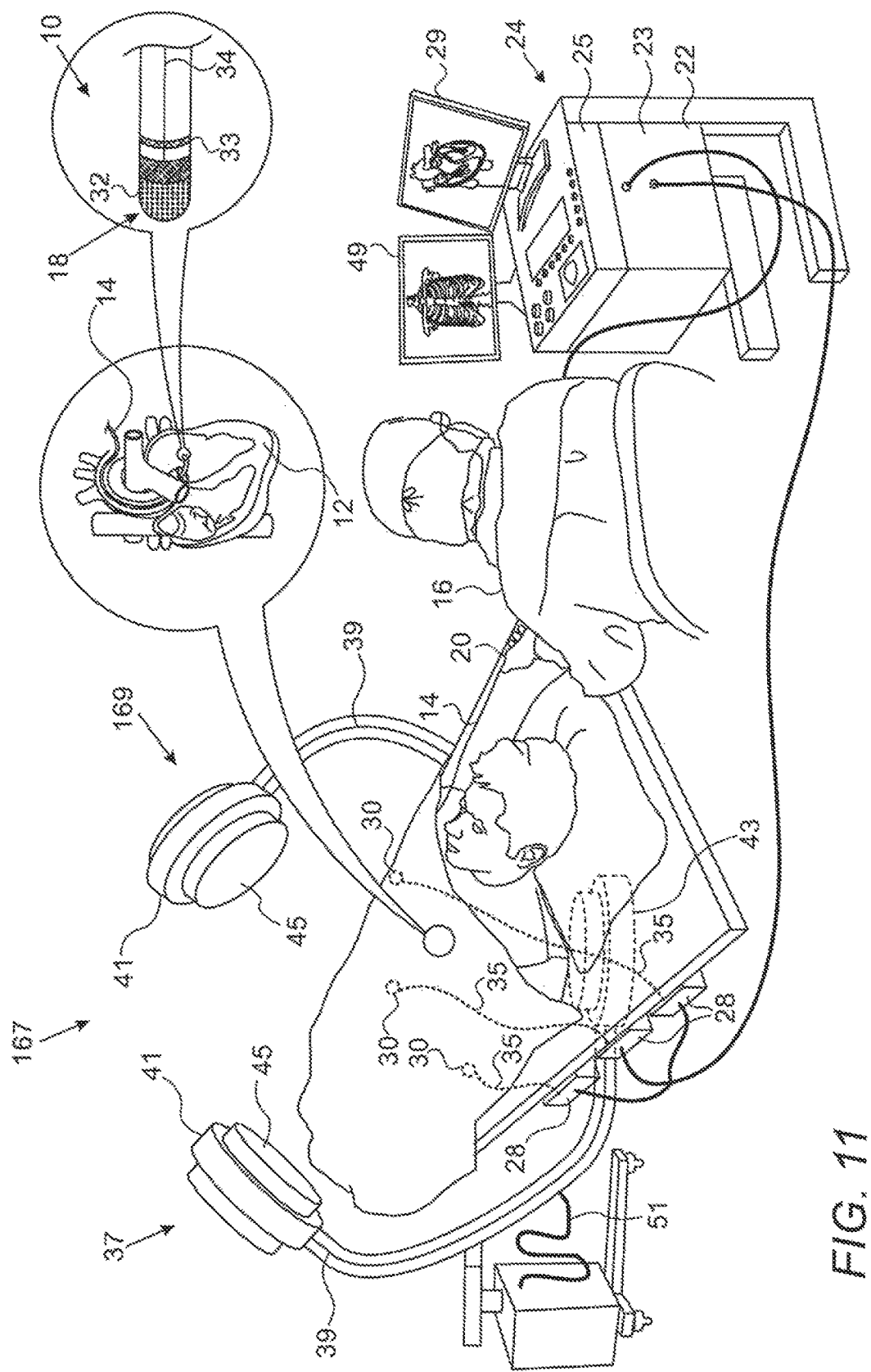
FIG. 11 is a pictorial illustration of a system for performing ablative procedures on a heart of a living subject, which is constructed and operative in accordance with an alternate embodiment of the invention.

Reference is now made to FIG. 11, which is a pictorial illustration of a system 167 for performing ablative procedures on a heart of a living subject, which is constructed and operative in accordance with an alternate embodiment of the invention. The system 167 is similar to the system 10 (FIG. 1), except now there are two fluoroscopic imaging devices 37, 169, which are directed at the heart 12, one at each of the primary angles. The fluoroscopic imaging devices 37, 169 may image the heart in the left anterior oblique and right anterior oblique views simultaneously. An advantage of this embodiment is minimization of delay in acquiring the fluoroscopic images. Because images are acquired synchronously, synchronization step 65 (FIG. 2) can be omitted.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method, comprising the steps of:
introducing a catheter into a coronary sinus of a heart of a living subject;
while the catheter is in the coronary sinus acquiring a first set of frames at first and second primary angles, the first set of frames comprising 2-dimensional images of the catheter using an imaging device;
thereafter acquiring a second set of frames at first and second primary angles, the second set of frames comprising 2-dimensional images of the catheter using the imaging device;
establishing respective 2-dimensional models of the catheter in frames of the first set and the second set, the 2-dimensional models comprising respective tracked 2-dimensional paths of the catheter;
synchronizing the first set with the second set by identifying a first pair of frames from the first set and the second set taken at the first primary angle and a second pair of frames from the first set and the second set taken at the second primary angle that are in respective phases of a cardiorespiratory cycle;
constructing first and second 3-dimensional models of the catheter from the synchronized frames using the respective 2-dimensional models;
geometrically transforming the first and second 3-dimensional models to minimize a distance function there between; and
displaying the transformed 3-dimensional models;
wherein the subject has a sagittal plane and wherein the steps of acquiring the first set and acquiring the second set each comprise acquiring frames at a first primary angle and at a second primary angle with the sagittal plane; and
wherein the difference between first and second primary angles varies by up to 120°.

2. The method according to claim 1, wherein geometrically transforming comprises applying a rotation matrix and a translation vector to one of the first and second 3-dimensional models and displaying comprises superimposing the transformed 3-dimensional models.

3. The method according to claim 1, wherein the first primary angle is 30° and the second primary angle is −30° with the sagittal plane.

4. The method according to claim 1, further comprising acquiring frames at the first primary angle and the second primary angle simultaneously.

5. The method according to claim 1 wherein said step of establishing respective 2-dimensional models comprises the steps of:
filtering the first set and the second set of frames;
sampling a corridor about a catheter path in the filtered frames; and
thereafter determining an optimal path of the catheter in the filtered frames.

6. The method according to claim 5, wherein filtering comprises performing a fast radial transform on a determinant of a hessian of the synchronized frames.

7. The method according to claim 5, wherein filtering comprises applying monogenic filters on a determinant of a hessian of the synchronized frames.

8. The method according to claim 5, wherein filtering comprises applying matched filters to tubes in the synchronized frames.

9. The method according to claim 1, wherein constructing first and second 3-dimensional models comprises:
constructing a chain of linear 3-dimensional segments connected by joints; and
calculating 3-dimensional coordinates of the joints so as to minimize a deviation of a projection of the 3-dimensional segments onto the respective tracked 2-dimensional paths.

10. The method according to claim 9, wherein the steps of constructing a chain and calculating 3-dimensional coordinates are performed iteratively.

11. The method according to claim 9, wherein establishing respective 2-dimensional models comprises the steps of tracking a tip of the catheter in the synchronized frames, and constructing first and second 3-dimensional models comprises initializing 3-dimensional coordinates of the tip.

12. The method according to claim 1, wherein constructing first and second 3-dimensional models comprises the steps of:
defining a plurality of 3-dimensional points as intersections of respective projection rays;
fitting a 3-dimensional spline to the 3-dimensional points to define a 3-dimensional path;
projecting the 3-dimensional path onto one of the 2-dimensional models; and
modifying the 3-dimensional path to minimize the distance function between the projected 3-dimensional path and the one 2-dimensional model.

13. The method according to claim 1, wherein the imaging device is a fluoroscopic imaging device.

14. An apparatus, comprising:
a cardiac catheter adapted for introduction into a coronary sinus of a heart of a living subject;
a display; and
a processor, which is cooperative with an imaging device for performing the steps of:
while the catheter is in the coronary sinus activating the imaging device to acquire a first set of frames comprising 2-dimensional images of the catheter and thereafter acquiring a second set of frames comprising 2-dimensional images of the catheter using the imaging device;
establishing respective 2-dimensional models of the catheter in frames of the first set and the second set, the 2-dimensional models comprising respective tracked 2-dimensional paths of the catheter;

synchronizing the first set with the second set by identifying a first pair of frames from the first set and the second set taken at the first primary angle and a second pair of frames from the first set and the second set taken at the second primary angle that are in respective phases of a cardiorespiratory cycle;

constructing first and second 3-dimensional models of the catheter from the synchronized frames using the respective 2-dimensional models;

geometrically transforming the first and second 3-dimensional models to minimize a distance function there between; and displaying the transformed 3-dimensional models on the display wherein the subject has a sagittal plane and the imaging device acquires the first set and the second set at a first primary angle and at a second primary angle with the sagittal plane; and wherein the difference between the first and second primary angles varies by up to 120°.

15. The apparatus according to claim 14, wherein the subject has a sagittal plane and the first primary angle is 30° and the second primary angle is −30° with the sagittal plane.

16. The apparatus according to claim 14, wherein the imaging device is operative for acquiring the first set and the second set at the first primary angle and the second primary angle simultaneously.

17. The apparatus according to claim 14, wherein establishing respective 2-dimensional models in one of the synchronized frames comprises sampling a corridor about a catheter path of another of the synchronized frames and determining an optimal path in the one synchronized frame for the corridor.

18. The apparatus according to claim 14, wherein establishing respective 2-dimensional models comprises performing a fast radial transform on a determinant of a hessian of the synchronized frames.

19. The apparatus according to claim 14, wherein establishing respective 2-dimensional models comprises applying monogenic filters on a determinant of a hessian of the synchronized frames.

20. The apparatus according to claim 14, wherein establishing respective 2-dimensional models comprises applying matched filters to tubes in the synchronized frames.

21. The apparatus according to claim 14, wherein constructing first and second 3-dimensional models comprises:
constructing a chain of linear 3-dimensional segments connected by joints; and
calculating 3-dimensional coordinates of the joints so as to minimize a deviation of a projection of the 3-dimensional segments onto the respective tracked 2-dimensional paths.

22. The apparatus according to claim 21, wherein the steps of constructing a chain and calculating 3-dimensional coordinates are performed iteratively.

23. The apparatus according to claim 21, wherein establishing respective 2-dimensional models comprises the steps of tracking a tip of the catheter in the synchronized frames, and constructing first and second 3-dimensional models comprises initializing 3-dimensional coordinates of the tip.

24. The apparatus according to claim 14, wherein constructing first and second 3-dimensional models comprises the steps of:
defining a plurality of 3-dimensional points as intersections of respective projection rays;
fitting a 3-dimensional spline to the 3-dimensional points to define a 3-dimensional path;
projecting the 3-dimensional path onto one of the 2-dimensional models; and
modifying the 3-dimensional path to minimize the distance function between the projected 3-dimensional path and the one 2-dimensional model.

25. The apparatus according to claim 14, wherein the imaging device is a fluoroscopic imaging device.

* * * * *